United States Patent [19]

Gunkel et al.

[11] Patent Number: 5,206,404
[45] Date of Patent: Apr. 27, 1993

[54] TRIARYL PHOSPHATE ESTER COMPOSITION AND PROCESS FOR ITS PREPARATION

[75] Inventors: Louis T. Gunkel, Yardley; Douglas G. Placek, Fairless Hills; Michael P. Marino, Jr., Radnor, all of Pa.; John Crosby, Lawrenceville; Sundeep G. Shankwalkar, East Brunswick, both of N.J.

[73] Assignee: FMC Corporation, Philadelphia, Pa.

[21] Appl. No.: 873,867

[22] Filed: Apr. 27, 1992

[51] Int. Cl.$^5$ .............................................. C07F 9/12
[52] U.S. Cl. .................................... 558/146; 558/211
[58] Field of Search ................................ 558/211, 146

[56] References Cited

U.S. PATENT DOCUMENTS

| | | | |
|---|---|---|---|
| Re. 29,540 | 2/1978 | Randell et al. | 260/966 |
| 2,071,323 | 2/1937 | Bass | 260/99.2 |
| 3,071,549 | 1/1963 | Stark | 252/78 |
| 3,432,437 | 3/1969 | Nail | 252/78 |
| 3,931,023 | 1/1976 | Dounchis | 252/49.8 |
| 3,945,891 | 3/1976 | Aal et al. | 203/77 |
| 3,992,309 | 11/1976 | Dounchis | 252/49.8 |
| 4,016,048 | 4/1977 | Gehrmann et al. | 203/49 |
| 4,087,386 | 5/1978 | Dounchis | 252/49.8 |
| 4,093,680 | 6/1978 | Randell et al. | 260/966 |
| 4,171,272 | 10/1979 | Wright | 252/46.7 |
| 4,227,972 | 10/1980 | Hernandez et al. | 203/37 |
| 4,414,161 | 11/1983 | Giolito | 260/975 |
| 4,645,615 | 2/1987 | Drake | 252/78.5 |

OTHER PUBLICATIONS

Perry et al., *Chemical Engineer's Handbook*, 5th Ed., McGraw-Hill (1973) pp. 13-55 to 13-60.
Eckles et al., "When to Use High Vacuum Distillation," *Chemical Engineering*, May 1991, pp. 201-203.
Kirk-Othmer, *Encyclopedia of Chemical Technology*, 3rd Ed., vol. 9, John Wiley & Sons, N.Y. (1980) pp. 478-481.
FMC, PRS-110 Phosphate Ester, Technical Data Sheet May 1991.

*Primary Examiner*—Mary C. Lee
*Assistant Examiner*—Michael G. Ambrose
*Attorney, Agent, or Firm*—R. E. Elden; F. Ianno; R. L. Andersen

[57] ABSTRACT

The invention is a novel composition of alkylated phenyl phosphate esters comprising by weight 1% to 20% trialkylphenyl phosphate, 10% to 50% dialkylphenyl monophenyl phosphate, 15% to 60% monoalkylphenyl diphenyl phosphate and less than 2% triphenyl phosphate and a process for preparing the composition comprising passing the composition at least once through a thin film evaporator at a temperature of about 200° C. to about 250° C. at a pressure sufficiently less than 5 kPa to evaporate about 5% to about 30% of the composition.

12 Claims, No Drawings

TRIARYL PHOSPHATE ESTER COMPOSITION AND PROCESS FOR ITS PREPARATION

The invention is a novel liquid mixed triaryl phosphate composition containing a reduced concentration of triphenyl phosphate and a process for its manufacture.

Mixed synthetic triaryl phosphate esters are prepared by alkylating phenol with alkenes such as propylene or isobutylene to obtain a mixture of phenol and substituted phenols. According to U.S. Pat. No. 4,093,680 this alkylate mixture is then reacted with phosphorus oxychloride (POCl$_3$) to form a mixed triaryl phosphate ester. The product mix is a statistical mixture based on the composition of the starting alkylate and always includes some fraction of triphenyl phosphate (TPP), usually from 5 to 50 percent. The product's physical properties are determined by the degree of alkylation of the phenol. A highly alkylated phenol mixture will result in a more viscous phosphate ester product than one less substituted For example, this process results in products that are a mixture of phosphate ester isomers including: triphenyl phosphate, diphenyl alkylphenyl phosphate, phenyl di(alkylphenyl)phosphate, and tri(alkylphenyl)phosphate ("mixed alkylated phosphate esters"). It is also possible that phenol rings with 2-5 alkyl groups may be present, however, these groups are slow to react with POCl$_3$, and are present at less than 0.5% in commercial products. The final product is tailored by selecting a specific blend of phenol and alkyl phenols as starting materials.

Such phosphate esters are used as fire resistant lubricant basestocks, lubricant anti-wear additives, and flame retardant plasticizers. A phosphate ester that is highly, resistant to oxidative, thermal, and hydrolytic degradation is desirable. In addition, a phosphate ester that has low volatility will not exhibit large evaporation losses, which is advantageous for high temperature applications.

Prior phosphate esters with good oxidative stability had poor hydrolytic stability, and conversely, phosphate esters with good hydrolytic stability had reduced oxidative stability. It is desirable to produce a triaryl phosphate ester with a combination of excellent thermal, oxidative, and hydrolytic stability.

The present invention overcomes the problems of the prior art by providing a fluid composition of mixed alkylated triphenyl phosphate esters comprising by weight 1% to 20% trialkylphenyl phosphate, 10% to 50% dialkylphenyl monophenyl phosphate, 15% to 60% monoalkylphenyl diphenyl phosphate and less than 2% triphenyl phosphate, wherein the alkyl moieties are selected from the group consisting of isopropyl, isobutyl, tertiary-butyl, isoamyl and tertiary-amyl.

The composition may be prepared from mixed alkylated triphenyl phosphate ester compositions, such as one prepared by alkylating phenol and reacting the phenol with phosphorus oxychloride to provide a composition of mixed alkylated triphenyl phosphate esters also containing from about 5% to about 50% by weight unalkylated triphenyl phosphate, the process comprising passing the composition at least once through a thin film evaporator, concomitantly agitating the surface of the composition and heating the composition at a temperature of about 200° C. to about 250° C. at a pressure sufficiently less than 5 kPa to evaporate about 5% to about 30% of the composition and withdrawing the residue as product without substantial condensation of vapor into the residue, thereby reducing the concentration of unalkylated triphenyl phosphate in the product.

Desirably the process is part of an overall process for manufacturing mixed alkylated phosphate esters by the steps of alkylating phenol to a mixture of phenol and alkylated phenol, reacting the mixture of phenol and alkylated phenol with phosphorus oxychloride to form a composition of mixed alkylated triphenyl phosphate esters containing from about 5% to about 50% by weight unalkylated triphenyl phosphate, the improvement comprising passing the composition at least once through a thin film evaporator and concomitantly agitating the surface of the composition and heating the composition at a temperature of about 200° C. to about 250° C. at a pressure sufficient to evaporate about 5% to about 30% of the composition as vapor and withdrawing the residual mixed alkylated triphenyl phosphate ester from the thin film evaporator as product without substantial condensation of vapor therein, thereby producing a mixed alkylated triphenyl phosphate ester product with a reduced concentration of unalkylated triphenyl phosphate therein.

It is possible to alkylate phenol completely and then react this mixture with POCl$_3$ to form a phosphate ester that is free of triphenyl phosphate but a product with more than 65% of the phenol alkylated would be extremely viscous or perhaps even a solid and would not meet the specifications in the fluids applications that this particular product is designed for.

The TPP can be removed by fractional distillation (under vacuum) and recovering the portion of the ester that remains in the reboiler. The product is desirable as a more stable fluid product with respect to both thermal and hydrolytic stability. However, the product recovered from the reboiler is unsatisfactory because of excessive color and acidity. For example, it was found in one example that the product darkened from a light colored starting material (60 APHA) to a dark brown liquor resembling coffee. The acidity of the material also doubled during the distillation. Further, it was found to be necessary to distill off half of the feed in the rectification still in order to remove most of the triphenyl phosphate from the starting mixture of phosphate esters containing 17% TPP, probably because the boiling points of the phosphate esters are not very different, the higher molecular weight esters (i.e. more substituted phenol groups) being only slightly higher boiling, and thereby are not easy to separate.

Because of the viscosity of the mixed alkylated triphenyl phosphate esters (TAP) and the high boiling points of the components thereof, it is important that the vapor be evaporated when the TAP is present on the heat exchange surface as a thin film, the surface of which is continuously renewed. For example, by means of a cascading or falling film evaporator, or an evaporator providing mechanical spreading, such as a centrifugal or wiped film evaporator, preferably a wiped film evaporator.

Running the TAP through a wiped film evaporator does not seem a likely way to fractionate the product because there is very little rectification involved in shortpath distillation (in a wiped film or thin film evaporator). In fact, running the material through a wiped film evaporator to effect a 50/50 split resulted in no significant rectification and enriched the overhead portion only slightly in TPP and the TPP content in the residue was still 9.5%. It was found to be necessary to lower the wall temperature of the wiped film evaporator to a minimum temperature and to control the vacuum and feed rate such that only 5% to 30% and preferably 15% to 20% of the feed is flashed overhead. In this manner the triphenyl phosphate (TPP) content of the residue is substantially reduced in a single pass. By passing the product through such an evaporator two or more times it is possible to reduce the TPP content to less than 2% by weight. Further, the color of the product is found to increase only to the extent expected by the concentration while there is substantially no increase in the product acidity as measured by the acid number.

Generally, the temperature of the evaporator surface should be controlled between 200° C. and 250° C. and the absolute pressure in the evaporator should be less than 5 kPa.

Although the hydrolytic stability of any C3 to C5 alkylated TAP can be improved by the present process, unexpectedly superior thermal and hydrolytic stability properties are obtained when the alkyl moiety is a tertiary alkyl, preferably a t-butyl moiety. The scope of this invention is not limited to a single alkyl moiety but is intended to include mixed esters produced by reacting $POCl_3$ with mixtures of phenol alkylates with any C3 to C5 alkene.

However, the mixed t-butylphenyl phosphate esters produced by this process containing 1% or less triphenyl phosphate are a particularly preferred product useful as a high stability base fluid that can be used as a fire resistant hydraulic fluid, compressor fluid, gas turbine oil, fire resistant grease basestock, or refractory binder. Such an ashless anti-wear base stock with excellent overall stability is particularly desirable for critical applications like jet engine lubricants, aircraft hydraulic fluids, metalworking lubricants, gear oils, greases, industrial hydraulic fluids, engine oils, transmission fluids, compressor lubricants, and universal tractor fluids.

The reduced volatility of the low product is desirable for any high temperature application, where the product is used as a lubricant additive, lubricant base fluid, or low volatility plastic flame retardant plasticizer.

Having described the best mode of practicing the invention, the following examples are presented to illustrate variations and modifications which can be made by one skilled in the art but not as limitations.

TEST METHODS

Hydrolytic stability was measured by ASTM test D2619-83 in which the sample of 75 g of fluid plus 25 g of water and a copper test specimen are sealed in a pressure-type beverage bottle. The bottle is rotated, end for end, for 48 hours in an oven at 93° C. Layers are separated, and insolubles are weighed. Weight change of copper is measured. Viscosity and acid number changes of fluid and acidity of water layer are determined.

Oxidative stability was determined according to ASTM test E537-86 which utilizes techniques of differential thermal analysis (DTA) and differential scanning calorimetry (DSC).

Anti-wear properties of lubricants was determined by the ASTM D2266 4-ball wear test.

Volatility was determined by the ASTM-3850-84 thermogravimetric (TGA) test.

For convenience in the examples specific mixed alkylated triphenyl phosphate esters are designated phenyl/t-butylphenyl phosphate (or phenyl/isopropylphenyl phosphate etc.).

COMPARATIVE EXAMPLE A

Batch Distillation of Mixed Phenyl/t-butylphenyl Phosphate Ester

One thousand grams of a commercial phenyl/t-butylphenyl triaryl phosphate ester were charged to a 2000 ml round bottomed flask equipped for distillation with a twelve inch flask jacketed one inch diameter column filled with Goodloe wire mesh packing. The pressure was reduced to 1 mm Hg and the batch distillation was started. The pot temperature was 270° C. during the distillation. The overhead temperature started at 187° C. and was 225° C. after four hours when the distillation was finished. The pot was sampled periodically for TPP content. The distillate weighed 506 grams and the residue product was 493 grams. The product had darkened considerably in color and the acidity had doubled from 0.1 to 0.2 mgKOH/gm.

The properties of the feed, overheads and product are shown in Table I. Although the triphenyl phosphate (TPP) content was reduced to less than 0.5% the increase in acid number and color was undesirable.

EXAMPLE 1

Wiped Film Evaporation of Mixed Phenyl/t-ButylPhenyl Phosphate Ester

The mixed phenyl/t-butylphenyl triaryl phosphate ester containing 17.0% triphenyl phosphate of Example A was subjected to single pass through a wiped film evaporator in an attempt to reduce the TPP content of the underflow portion. A wiped film still with 323 square centimeters of evaporative area was employed. The feed was heated to 200° C. The film wall temperature was 250° C. and the system pressure 1.0 mm Hg.

One hundred and sixteen grams of the mixed phenyl/t-butylphenyl phosphate were fed through the wiped film evaporator over 120 minutes. The overhead weighed 62 grams (52%) and contained 22.0% TPP while the underflow weighed 54 grams (48%) and contained 9.5% TPP.

This separation was unexpected when one considers the fractionation and long distillation times required in the Example A, batch distillation. Normally wiped film evaporators are used to effect easy separations such as taking small amounts of solvents from a product or separating the major portion of a product from a much higher boiling residue or impurity. The short path of a wiped film or falling film evaporator does not normally provide much, if any, rectification for relatively close boiling compounds as here. The vapor pressure data for triphenyl phosphate is quite similar to that derived for the mixed t-butylphenyl phosphate ester employed here (see Table III).

EXAMPLE 2

Wiped Film Evaporation of Mixed Phenyl/t-ButylPhenyl Phosphate Ester

A mixed phenyl/t-butylphenyl triaryl phosphate ester containing 17.0% triphenyl phosphate (TPP) was subjected to repeated passes through a wiped film evaporator in an attempt to reduce the TPP content of the underflow portion. A wiped film evaporator with 323 square centimeters of evaporative area was employed. The feed was heated to 200° C. The film wall temperature was 230° C. and the system pressure 1.0 mm Hg.

Pass I

Eight hundred and eighty-five grams of mixed phenyl/t-butylphenyl phosphate were fed through the wiped film still over 141 minutes. The overhead weighed 199 grams (22%) and contained 39.0% TPP while the underflow weighed 684 grams (78%) and contained 10.4% TPP.

Pass II

The underflow from Pass I was rerun through the still over an 80 minute period. The overhead weighed 215 grams (32%) and contained 24.6% TPP while the underflow weighed 459 grams (68%) and contained 4.5% TPP.

Pass III

The bottoms from Pass II were then run through the still at a rate of 8 grams per minute. The overhead weighed 95 grams (21%) and contained 13.1% TPP while the underflow weighed 352 grams (79%) and contained 1.2% TPP.

In three passes through the still it is possible to lower the TPP content to less than 2% while still maintaining product color and acidity (see Table II).

This separation is remarkable in that the vapor pressure of triphenyl phosphate and the mixed t-butylphenyl phosphate are very close as illustrated in Table III.

EXAMPLE 3

Wiped Film Evaporation of Mixed Phenyl/t-Butylphenyl Phosphate Ester

In this example, nine hundred grams of a phenyl/t-butylphenyl mixed phosphate ester containing 41.6% of triphenyl phosphate were passed through a wiped film evaporator with 323 square cm of evaporative surface a number of times to reduce the TPP content in the underflow to less than 2%. The system pressure was 1.0 mm Hg and the wall temperature of the still was 233° C.

Pass I

The feed time for the first pass was 120 minutes. The overhead weighed 368 grams (40%) and contained 62.0% TPP while the underflow weighed 536 grams (60%) and contained 28.2% TPP.

Pass II

The underflow from Pass I was then refed through the unit over a 60 minute period. The overhead weighed 160 grams (30%) and contained 50.5% TPP while the underflow weighed 370 grams (70%) and contained 19.0% TPP.

Pass III

The underflow from Pass II was put through the still over a 50 minute period. The overhead weighed 125 grams (35%) and contained 33.9% TPP while the underflow weighed 235 grams (65%) and contained 10.3% TPP.

Pass IV

The underflow from Pass III was then rerun through the still in 30 minutes. The overhead weighed 47 grams (20%) and contained 23.7% TPP while the underflow weighed 186 grams (80%) and contained 4.1% TPP.

Pass V

Pass IV underflow was put through the still in 25 minutes. The overhead weighed 33 grams (18%) and contained 12.8% TPP while the underflow weighed 152 grams (82%) and contained 1.3% TPP.

The triphenyl phosphate content of a product containing 41% TPP was reduced to 1.3% without adverse effect on the product color or acidity. The distillate or overhead fractions can be blended back into other products where TPP content is desired.

EXAMPLE 4

Wiped Film Evaporator Distillation of Mixed Phenyl/Isopropyl Phenyl Phosphate Ester Eight Hundred and sixty-eight grams of a mixed phenyl/isopropyl phenyl phosphate ester containing 7.64% triphenyl phosphate were passed through a wiped film still with 323 square cm of evaporative area over a period of 80 minutes. The system pressure was 0.5 mm Hg and the film wall temperature was 232° C. The feed was preheated to 200° C.

Pass I

The split of the first pass was as follows: The overhead weighed 189 grams (22%) and contained 15.5% TPP while the underflow weighed 675 grams (78%) and contained 5.5% TPP.

Pass II

The underflow from the first pass was then run through the still. Six hundred and sixty-six grams were fed over 70 minutes at the same operating conditions. The results were: The overhead weighed 129 grams (19%) and contained 11.8% TPP while the underflow weighed 546 grams (81%) and contained 3.1% TPP.

Pass III

The underflow from the second pass was put through the wiped film still under the same operating conditions. Five hundred and forty-four grams were fed over 60 minutes. The overhead weighed 134 grams (24%) and contained 8.7% TPP while the underflow weighed 407 grams (76%) and contained 1.4% TPP.

Thus after three passes, requiring only a total of 10 minutes residence time at temperature in the still, the triphenyl phosphate content of the ester was reduced to the desired 1–2% level. Color of the bottoms product did not increase during the process.

EXAMPLE 5

A commercial t-butylphenyl phosphate ester was distilled to produce as product the invention claimed, which was designated PRS-110. The starting material contained 17.0% TPP. After evaporation in a wiped film evaporator the product contained by weight 0.50% triphenyl phosphate (TPP), 33.2% diphenyl t-butylphenyl phosphates, 49.5% phenyl di(t-butylphenyl) phosphates and 12.5% tri(t-butylphenyl) phosphates.

Other properties include: 7.0% phosphorus content, 107.5 viscosity, cSt @100° F., 7.81 viscosity, cSt @210° F. and 1.11 specific gravity @20°/20° C.

Unexpectedly, the composition had improved physical properties, compared to typical values for other triaryl phosphate esters as shown in Tables IV (Oxidative Stability), V (Hydrolytic Stability) and VI (Four Ball Wear). The product did have the expected reduced volatility.

TABLE I
ANALYSIS OF STARTING MATERIAL AND DISTILLATION FRACTIONS OF MIXED t-BUTYLPHENYL PHOSPHATE COMPARATIVE EXAMPLE A

| Property | Starting Material | Overhead Fraction | Product |
|---|---|---|---|
| Color | 60 APHA | 55 APHA | >500 APHA |
| Acid Number | 0.11 | 0.12 | 0.21 |
| Sp.G @ 20° C. | 1.13 | 1.14 | 1.11 |
| Viscosity | | | |
| CS @ 37.7° C./100° F. | 47.7 | 27.76 | 107.50 |
| CS @ 98.9° C./210° F. | 5.44 | 4.17 | 7.81 |
| Moisture % | 0.084 | 0.015 | 0.015 |
| $P_4$ Content* | 7.6 | 7.9 | 7.0 |
| GC Analysis | | | |
| TPP | 17.0 | 34.7 | 0.50 |
| DPBPP | 43.4 | 47.8 | 33.2 |
| PDBPP | 30.1 | 10.5 | 49.5 |
| TBPP | 5.4 | 0.3 | 12.5 |

*$P_4$ content calculated from GC analysis.

TABLE II
ANALYSIS OF STARTING MATERIAL AND PRODUCT FROM THE WIPED FILM EVAPORATION EXAMPLE 2

| Property | Starting Material | Product |
|---|---|---|
| Color | 60 APHA | 70–80 APHA |
| Acid Number | 0.11 MgKOH/gm | 0.09 MgKOH/gm |
| Sp.G. @ 20° C. | 1.13 | 1.108 |
| Viscosity | | |
| CS @ 100° F. | 47.7 | 103.8 |
| CS @ 210° F. | 5.44 | 7.58 |
| Moisture % | 0.084 | 0.01 |
| $P_4$ Content* | 7.6 | 7.0 |
| GC Analysis - Area % | | |
| TPP | 17.0 | 1.2 |
| DPBPP | 43.4 | 34.0 |
| PDBPP | 30.1 | 49.8 |
| TBPP | 5.4 | 13.6 |

*$P_4$ content calculated from GC analysis

TABLE III
VAPOR PRESSURE DATA FOR TRIPHENYL PHOSPHATE

| | Vapor Temperature, °C. | |
|---|---|---|
| Pressure, mm Hg | Triphenyl Phosphate | Comm. t-butylphenyl phosphate* |
| 1.0 | 193.5 | 214.0 |
| 5.0 | 230.4 | 246.1 |
| 10.0 | 249.8 | 269.3 |
| 20.0 | 269.7 | 288.5 |
| 50.0 | 297.8 | 316.0 |
| 100.0 | 322.5 | 338.7 |
| 200.0 | 349.8 | 363.3 |

*commercial mixed t-butylphenyl phosphate containing 17% triphenyl phosphate

TABLE IV
OXIDATIVE STABILITY OF PHOSPHATE ESTERS AS MEASURED BY DIFFERENTIAL SCANNING CALORIMETRY (DSC) ACCORDING TO ASTM D-3350

| Commercial Product | Oxidation Onset Temp. °C. |
|---|---|
| Tri-n-butyl phosphate | 175 |
| Tris(2-ethylhexyl)phosphate | 160 |
| Tricresyl phosphate | 215 |
| Trixylenyl phosphate | 210 |
| Isopropylphenyl phosphate (ISO 46 viscosity grade) | 210 |
| Isopropylphenyl phosphate (ISO 68 viscosity grade) | 215 |
| t-butylphenyl phosphate (ISO 32 viscosity grade) | 300 |
| t-butylphenyl phosphate (ISO 46 viscosity grade) | 300 |
| Example 5 product t-butylphenyl phosphate (ISO 100 viscosity grade) | 310 |

ISO = International Standards Organization

TABLE V
HYDROLYTIC STABILITY AS MEASURED BY ASTM D-2619

| | Copper | Acidity | |
|---|---|---|---|
| Commercial Product | Wt. Loss mg/cm$^2$ | Oil Layer mg KOH/g | Water Layer mg KOH |
| Tri-n-butyl phosphate | 1.37 | 0.0 | 72.9 |
| Tris(2-ethylhexyl) phosphate | 1.11 | 0.27 | 4.84 |
| Tricresyl phosphate | 0.3 | 0.10 | 9.1 |
| Trixylenyl phosphate | 0.03 | 0.0 | 0.0 |
| Isopropylphenyl phosphate (ISO 32 viscosity grade) | 1.12 | 0.05 | 24.6 |
| Isopropylphenyl phosphate (ISO 46 viscosity grade) | 0.05 | 0.03 | 4.5 |
| t-butylphenyl phosphate (ISO 32 viscosity grade) | 0.25 | 0.26 | 38.7 |
| t-butylphenyl phosphate (ISO 46 viscosity grade) | 0.18 | 0.05 | 6.17 |
| Example 5 product t-butylphenyl phosphate (ISO 100 viscosity grade) | 0.04 | 0.13 | 1.30 |

ISO = International Standards Organization

TABLE VI
FOUR BALL WEAR TEST AND WEIGHT LOSS COMPARISON WITH COMMERCIAL PHOSPHATE ESTERS

| Product | ASTM D-2266 4 Ball Wear-mm | ASTM D-3850 1% Weight Loss °C. |
|---|---|---|
| Tricresyl phosphate | 0.60 | 184 |
| Isopropylphenyl phosphate (ISO 41) | 0.60 | 201 |
| t-butylphenyl phosphate (ISO 32) | 0.60 | 227 |
| Product - Example 5 | 0.52 | 235 |

We claim:

1. A composition of mixed alkylated triphenyl phosphate esters comprising by weight 1% to 20% trialkylphenyl phosphate, 10% to 50% dialkylphenyl monophenyl phosphate, 15% to 60% monoalkylphenyl diphenyl phosphate and less than 2% triphenyl phosphate, wherein the alkyl moieties are selected from the group consisting of isopropyl, isobutyl, tertiary-butyl, isoamyl and tertiary-amyl.

2. The composition of claim 1 wherein substantially all of the alkyl moiety is tertiary-butyl.

3. The composition of claim 1 wherein substantially all of the alkyl moiety is isopropyl.

4. A process for purifying a composition of mixed alkylated triphenyl phosphate esters also containing from about 5% to about 50% by weight unalkylated triphenyl phosphate, the process comprising passing the composition at least once through a thin film evaporator, concomitantly agitating the surface of the composition and heating the composition at a temperature of about 200° C. to about 250° C. at a pressure sufficiently less than 5 kPa to evaporate about 5% to about 30% of the composition and withdrawing the residue as product without substantial condensation of vapor into the residue, thereby reducing the concentration of unalkylated triphenyl phosphate in the product.

5. The process of claim 4 wherein the concentration of unalkylated triphenyl phosphate is reduced to less than 2% by weight 6. The process of claim 4 wherein the thin film evaporator is a wiped film evaporator.

7. The process of claim 5 wherein the thin film evaporator is a wiped film evaporator.

8. The process of claim 4 wherein the product consists essentially of 1% to 20% by weight trialkylphenyl phosphate, 10% to 50% by weight dialkylphenyl monophenyl phosphate, 15% to 60% by weight monoalkylphenyl diphenyl phosphate and less than 2% by weight triphenyl phosphate.

9. In a process for manufacturing mixed alkylated phosphate esters by the steps of alkylating phenol to a mixture of phenol and alkylated phenol, reacting the mixture of phenol and alkylated phenol with phosphorus oxychloride to form a composition of mixed alkylated triphenyl phosphate esters containing from about 5% to about 50% by weight unalkylated triphenyl phosphate, the improvement comprising purifying the composition mixture by passing the composition at least once through a thin film evaporator and concomitantly agitating the surface of the composition and heating the composition at a temperature of about 200° C. to about 250° C. at a pressure sufficient to evaporate about 5% to about 30% of the composition as vapor and withdrawing the residual mixed alkylated triphenyl phosphate ester from the thin film evaporator as product without substantial condensation of vapor therein, thereby producing a mixed alkylated triphenyl phosphate ester product with a reduced concentration of unalkylated triphenyl phosphate therein.

10. The process of claim 9 wherein the concentration of unalkylated triphenyl phosphate is reduced to less than 2% by weight 11. The process of claim 9 wherein the thin film evaporator is a wiped film evaporator.

12. The process of claim 10 wherein the thin film evaporator is a wiped film evaporator.

* * * * *